(12) United States Patent
Wu et al.

(10) Patent No.: US 11,692,034 B2
(45) Date of Patent: Jul. 4, 2023

(54) CD47-CAR-T CELLS

(71) Applicants: ProMab Biotechnologies, Inc., Richmond, CA (US); Forevertek Biotechnology Co., Ltd, Hunan (CN)

(72) Inventors: Lijun Wu, Albany, CA (US); Vita Golubovskaya, Richmond, CA (US)

(73) Assignees: ProMab Biotechnologies, Inc., Richmond, CA (US); Forevertek Biotechnology Co., Ltd, Changsha (CN)

(*) Notice: Subject to any disclaimer, the term of this patent is extended or adjusted under 35 U.S.C. 154(b) by 923 days.

(21) Appl. No.: 16/521,421

(22) Filed: Jul. 24, 2019

(65) Prior Publication Data

US 2019/0338028 A1 Nov. 7, 2019

Related U.S. Application Data

(63) Continuation of application No. PCT/US2018/017672, filed on Feb. 9, 2018.

(60) Provisional application No. 62/458,773, filed on Feb. 14, 2017, provisional application No. 62/518,767, filed on Jun. 13, 2017, provisional application No. 62/546,790, filed on Aug. 17, 2017.

(51) Int. Cl.
*C07K 14/705* (2006.01)
*C07K 14/71* (2006.01)
*C07K 14/725* (2006.01)
*C07K 16/28* (2006.01)
*C12N 5/0783* (2010.01)

(52) U.S. Cl.
CPC ...... *C07K 16/2803* (2013.01); *C07K 14/7051* (2013.01); *C07K 14/70517* (2013.01); *C07K 14/70521* (2013.01); *C07K 14/70596* (2013.01); *C07K 14/71* (2013.01); *C07K 16/2839* (2013.01); *C07K 16/2863* (2013.01); *C07K 16/2896* (2013.01); *C12N 5/0636* (2013.01); *C07K 2317/24* (2013.01); *C07K 2317/31* (2013.01); *C07K 2317/56* (2013.01); *C07K 2317/622* (2013.01); *C07K 2317/76* (2013.01); *C07K 2319/02* (2013.01); *C07K 2319/03* (2013.01); *C07K 2319/30* (2013.01); *C12N 2510/00* (2013.01)

(58) Field of Classification Search
CPC .............. A61K 35/17; A61K 2039/505; A61K 39/395; A61K 39/001104; A61K 39/39558; C07K 2319/03; C07K 2317/622; C07K 2319/00; C07K 2319/33; C07K 2319/02; C07K 16/2896; C07K 14/70596; C07K 19/00; C07K 2317/53; C07K 2319/74; C07K 2317/565; C07K 2317/56; C07K 2319/71; C07K 16/28; C07K 16/2839; C07K 14/705
See application file for complete search history.

(56) References Cited

U.S. PATENT DOCUMENTS

| | | | | |
|---|---|---|---|---|
| 5,844,093 A | * | 12/1998 | Kettleborough | A61P 35/00 530/389.7 |
| 6,699,473 B2 | * | 3/2004 | Raisch | C07K 16/2863 424/1.49 |
| 9,017,675 B2 | * | 4/2015 | Liu | A61P 35/02 424/133.1 |
| 2013/0142786 A1 | | 6/2013 | Liu et al. | |
| 2016/0045551 A1 | | 2/2016 | Brentjens et al. | |
| 2019/0292258 A1 | * | 9/2019 | Lippincott | C07K 16/2803 |

FOREIGN PATENT DOCUMENTS

| WO | WO-2016109415 A1 | * | 7/2016 |
| WO | 2016130726 A1 | | 8/2016 |
| WO | WO-2017123675 A1 | * | 7/2017 |

OTHER PUBLICATIONS

Ahmad et al. scFv antibody: principles and clinical application. Clin Dev Immunol 2012: 980250, 2012.*
Asano et al. Highly effective recombinant format of a humanized IgG-like bispecific antibody for cancer immunotherapy with retargeting of lymphocytes to tumor cells. J Biol J Biol Chem 282(38): 27659-27665, 2007.*
Chang et al. CARs: synthetic immunoreceptors for cancer therapy and beyond. Trend Mol Med 23(5): 430-450, 2017.*
Guedan et al. Engineering and design of chimeric antigen recepors. Mol Ther: Methods Clin Dev 12: 145-156, 2019.*
Huang et al. Construction of CD47 specific CAR-NK and its anti-tumor activity in vitro. Eur J Immunol 46 (Suppl 1): 122, 2016.*
Kampmeier et al. Rapid optical imaging of EGF receptor expression with a single-chain antibody SNAP-tag fusion protein. Eur J Nucl Med Imaging 37: 1926-1934, 2010.*
Kaur et al. Preclinical and clinical development of therapeutic antibodies targeting functions of CD47 in the tumor microenvironment. Antibody Therapeutics 3(3): 179-192, 2020.*
Khantasup et al. Design and generation of humanized single-chain Fv derived from mouse hybridoma for potential targeting application. Monoclon Antib Immunodiagn Immunother 34(6): 404-417, 2015.*
Kikuchi et al. A bivalent single-chain Fc fragment against CD47 induces apoptosis for leukemic cells. Biochem Biophys Res Comm 315: 912-918, 2004.*

(Continued)

*Primary Examiner* — Bridget E Bunner
(74) *Attorney, Agent, or Firm* — Perkins Coie LLP; Viola Kung

(57) ABSTRACT

The present invention provides a chimeric antigen receptor (CAR) fusion protein comprising from N-terminus to C-terminus: (i) a single-chain variable fragment (scFv) comprising $V_H$ and $V_L$, wherein scFv has an activity against CD47, (ii) a transmembrane domain, (iii) at least one co-stimulatory domains, and (iv) an activating domain. In one embodiment, the scFv is derived from a humanized anti-CD47 antibody. The present invention also provides T cells modified to express the CAR of the present invention.

10 Claims, 11 Drawing Sheets

Specification includes a Sequence Listing.

(56) References Cited

OTHER PUBLICATIONS

Kikuchi et al. Apoptosis inducing bivalent single-chain antibody fragments against CD47 showed antitumor potency for multiple myeloma. Leukemia Res 29: 445-450, 2005.*

Lehmann et al. Stability engineering of anti-EGFR scFv antibodies by rational design of a lambda-to-kappa swap of the VL framework using a structure-guided approach. mAbs 7(6): 1058-1071, 2015.*

Rezaei et al. Development of anti-CD47 single-chain variable fragment targeted magnetic nanoparticles for treatment of human bladder cancer. Nanomed (Lond) 12(6): 597-613, 2017.*

Bhattacharya et al. Impact of genetic variation on three dimensional structure and function of proteins. PLoS One 12(3): e0171355, 2017.*

Bork, P. Powers and pitfalls in sequence analysis: the 70% hurdle. Genome Res 10: 398-400, 2000.*

Bork, P. Go hunting in sequence databases but watch out for the traps. Trends in Genetics 12(10): 425-427, 1996.*

Brenner. S.E. Errors in genome annotation. Trends in Genetics 15:132-133, 1999.*

Brorson et al. Mutational analysis of avidity and fine specificity of anti-levan antibodies. J Immunol 163: 6694-6701, 1999.*

Brummell et al. Probing the combining site of an anti-carbohydrate antibody by saturation-mutagenesis: role of the heavy-chain CDR3 residues. Biochem 32(4): 1180-1187, 1993.*

Burks et al. In vitro scanning saturation mutagenesis of an antibody binding pocket. Proc Natl Acad Sci USA 94: 412-417, 1997.*

Cassett et al. A peptide mimetic of an anti-CD4 monoclonal antibody by rationale design. Biochem Biophys Res Comm 307: 198-205, 2003.*

Chen et al. J Mol Biol 293: 865-881, 1999.*

Colman Research in Immunol. 145:33-36, 1994.*

De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*

Doerks et al. Protein annotation: detective work for function prediction. Trends in Genetics 14:248-250, 1998.*

Dotti et al. Design and development of therapies using chimeric angigen receptor-expressing T cells. Immunol Rev 257: 107-126, 2014.*

Fenton et al. Rheostat positions: a new classification of protein positions relevant to pharmacogenomics. Medicinal Chem Res 29: 1133-1146, 2020.*

Guo et al. Protein tolerance to random amino acid change. Proc Natl Acad Sci USA 101(25): 9205-9210, 2004.*

Holm et al. Functional mapping and single chain construction of the anti-cytokeratin 8 monoclonal antibody TS1. Mol Immunol 44: 1075-1084, 2007.*

Jang et al. The structural basis for DNA binding by an anti-DNA autobody. Mol Immunol 35: 1207-1217, 1998.*

Kobayashi et al. Tryptophan H33 plays an important role in pyrimidine (6-4) pyrimidone photoproduct binding by a high-affinity antibody. Protein Engineering 12(10): 879-884, 1999.*

MacCallum et al. Antibody-antigen interactions: contact analysis and binding site topography. J Mol Biol 262: 732-745, 1996.*

Ngo et al. "Computational complexity, protein structure prediction, and the Levinthal paradox" in The Protein Folding Problem and Tertiary Structure Prediction, pp. 492-495, 1994.*

Paul, William E., Fundamental Immunology, 3rd Edition, Raven Press, New York, Chapt. 8, pp. 292-295 (1993).*

Rudikoff et al. Single amino acid substitution altering antigen-binding specificity. Proc Natl Acad Sci USA 79: 1979-1983, 1982.*

Sela-Culang et al. The structural basis of antibody-antigen recognition. Front Immunol 4: 302, 2013 (13 total pages).*

Skolnick et al. From genes to protein structure and function: novel applications of computational approaches in the genomic era. Trends Biotechnol 18(1):34-39 2000.*

Smith et al. The challenges of genome sequence annotation or "the devil is in the details". Nature Biotechnol 15: 1222-1223, 1997.*

Tokuriki et al. Stability effects of mutations and protein evolvability. Curr Opin Structural Biol 19: 596-604, 2009.*

Vajdos et al. Comprehensive functional maps of the antigen-binding site of an anti-ErbB2 antibody obtained with shotgun scanning mutagenesis. J Mol Biol 320: 415-428, 2002.*

Vasudevan et al. A single amino acid change in the binding pocket alters specificity of an anti-integrin antibody AP7.4 as revealed by its crystal structure. Blood Cells Mol Diseases 32: 176-181, 2004.*

Wells, J.A. Additivity of mutational effects in proteins. Biochemistry 29(37): 8509-8517, 1990.*

Wu et al. Humanization of a murine monoclonal antibody by simultaneous optimization of framework and CDR residues. J Mol Biol 294: 151-162, 1999.*

Zhang et al. Comprehensize optimization of a single-chain variable domain antibody fragment as a targeting ligand for a cytotoxic nanoparticle. mAbs 7(1): 42-52, 2015.*

Vita Golubovskaya, et al., "CD47-CAR-T Cells Effectively Kill Target Cancer Cells and Block Pancreatic Tumor Growth", Cancers, Oct. 21, 2017, vol. 9(10), pii: E139.

Sukhbit Kaur, et al., "A function-blocking CD47 antibody suppresses stem cell and EGF signaling in triple-negative breast cancer", Oncotarget, 2016, vol. 7(9), p. 10133-52.

Michel Sadelain, et al., "The Basic Principles of Chimeric Antigen Receptor Design", Cancer Discov. 2013, vol. 3 (4), p. 388-98.

International Search Report dated Jul. 2, 2018 issued in PCT/US18/17672.

* cited by examiner

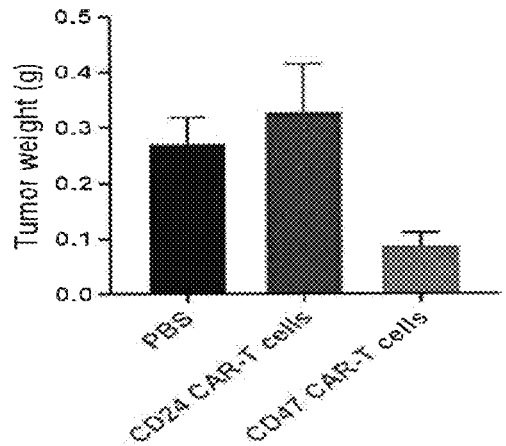

FIG. 4G

Mouse CD47 ScFv

\> VL-GBM00 VL B6H12       CDR1                        CDR2
DIVMTQSPATLSVTPGDRVSLSC*RASQTISD*YLHWYQQKSHESPRLLIK*FASQSIS*GIPSRFSGSGSGSDF
TLSINSVEPEDVGVYYC*QNGHGFPRTF*GGGTKLEIK
                  CDR3

\> VH-GBM00 VH B6H12            CDR1                       CDR2
EVQLVESGGDLVKPGGSLKLSCAASGFTFS*GYGMS*WVRQTPDKRLEWVA*TITSGGTYTYYPDSVKG*
RFTISRDNAKNTLYLQIDSLKSEDTAIYFCARS*LAGNAMDY*WGQGTSVTVSS
                              CDR3

Humanized CD47 ScFv

\> VL-GBM03               CDR1                    CDR2
EIVLTQSPATLSLSPGERATLSC*RASQSISD*YLHWYQQKPGQAPRLLIY*FASQRAT*GIPARFSGSGSGT
DFTLTISSLEPEDFAVYYC*QQGHGFPRTF*GGGTKVEIK
                  CDR3

\> VH-GBM03                   CDR1                       CDR2
EVQLVESGGGLVQPGGSLRLSCAASGFTFS*GYGMS*WVRQAPGKGLEWVA*TITSGGTYTYYPDSVK*
GRFTISRDNAKNSLYLQMNSLRAEDTAVYYCARS*LAGNAMDY*WGQGTLVTVSS
                           CDR3

FIG. 5A

CD47-CAR-T CELLS

This application is a continuation of PCT/US2018/017672, filed Feb. 9, 2018; which claims the priority of U.S. Provisional Application Nos. 62/458,773, filed Feb. 14, 2017; 62/518,767, filed Jun. 13, 2017, and 62/546,790, filed Aug. 17, 2017. The contents of the above-identified applications are incorporated herein by reference in their entireties.

REFERENCE TO SEQUENCE LISTING, TABLE OR COMPUTER PROGRAM

The Sequence Listing is concurrently submitted as an ASCII formatted text file via EFS-Web with a file name of Sequence Listing.txt with a creation date of Feb. 26, 2018, and a size of 26.1 kilobytes. The Sequence Listing filed via EFS-Web is part of the specification and is hereby incorporated in its entirety by reference herein.

FIELD OF THE INVENTION

The present invention relates to humanized CD47-CAR-T cells, which effectively attack tumor cells overexpressing CD47 tumor antigen.

BACKGROUND OF THE INVENTION

Immunotherapy is emerging as a highly promising approach for the treatment of cancer. T cells or T lymphocytes are the armed forces of our immune system that constantly look for foreign antigens and discriminates abnormal (cancer or infected cells) from normal cells. Genetically modifying T cells with CARs are a common approach to design tumor-specific T cells. CAR-T cells targeting tumor-associated antigens can be infused into patients (called adoptive T cell therapy) representing an efficient immunotherapy approach. The advantage of CAR-T technology compared with chemotherapy or antibody is that reprogrammed engineered T cells can proliferate and persist in the patient and work like a living drug.

CARs (Chimeric antigen receptors) usually consist of a monoclonal antibody-derived single-chain variable fragment (scFv) linked by a hinge and transmembrane domain to a variable number of intracellular signaling domains and a single, cellular activating, CD3-zeta domain. FIG. 1 shows the evolution of CARs from first generation (left, with no co-stimulation domains) to second generation (middle, with one co-stimulation domain CD28 or 4-BB) to third generation (with two or several co-stimulation domains), see Golubovskaya, Wu, Cancers, 2016 Mar. 15; 8(3). Generating CARs with multiple costimulatory domains (third generation CAR) have led to increased cytolytic activity, and significantly improved persistence of CAR-T cells that demonstrate augmented antitumor activity.

CD47 is a cell surface glycoprotein of the immunoglobulin superfamily that is often overexpressed in both hematological cancers (leukemia, lymphoma, see Chao et al., Cell, 2010, 142, 699-713, and multiple myeloma) and solid cancers such as ovarian, small cell lung cancer, pancreatic, glioma, glioblastoma, pediatric brain tumors and other types of cancers (Chao, supra, and Weiskopf, J. Clin. Invest. 2016, 126, 2610-2620). CD47 is also known as a "don't eat me signal" through binding to SIRP-α (signaling regulatory protein alpha) and blocking phagocytosis of tumor cells mediated by SIRP (Weiskopf, supra). High expression of CD47 has been shown to correlate with poor clinical outcomes in patients with hematological cancers such as non-Hodgkin lymphoma (Chao, supra) or acute myeloid leukemia (Majeti, et al., Cell, 2009, 138, 286-299) and also in solid tumors such as ovarian, glioblastoma, glioma, and others (Willingham, et al., Proc. Natl. Acad. Sci. USA 2012, 109, 6662-6667) and proposed to be a clinical prognostic factor. In addition, CD47 signaling has been shown to play a key role in maintenance of tumor initiating or cancer stem cells (Kaur, et al., Oncotarget, 2016, 7, 10133-10152). CD47 is highly expressed in cancer stem cells, the most aggressive type of tumor cells (Cioffi, et al., Clin. Cancer Res., 2015, 21, 2325-2337). Blocking interaction of CD47 and SIRP alpha on macrophages with CD47 induced phagocytosis of CD47-positive tumors Kim, et al., Leukemia 2012, 26, 2538-2545).

There exists a need for an improved adoptive T cell immunotherapy with improved efficacy and reduced toxicities.

BRIEF DESCRIPTION OF THE DRAWINGS

FIGS. 4F and 4G show CD47 CAR-T cells significantly decreased tumor size and weight, respectively. p<0.05, CD47-CAR-T cells versus control CD24-CAR-T cells and 1×PBS groups. Mouse tumors were analyzed by imaging (4F) and measuring weight in grams (4G).

FIG. 5A shows amino acid sequences of mouse and humanized CD47 ScFv. Upper panel. Mouse CD47 ScFv of B6H12 antibody (VL, SEQ ID NO: 5; VH, SEQ ID NO: 3). Lower panel: Humanized CD47 (VL, SEQ ID NO: 12; VH, SEQ ID NO: 11).

DETAILED DESCRIPTION OF THE INVENTION

Definitions

Figure 1:
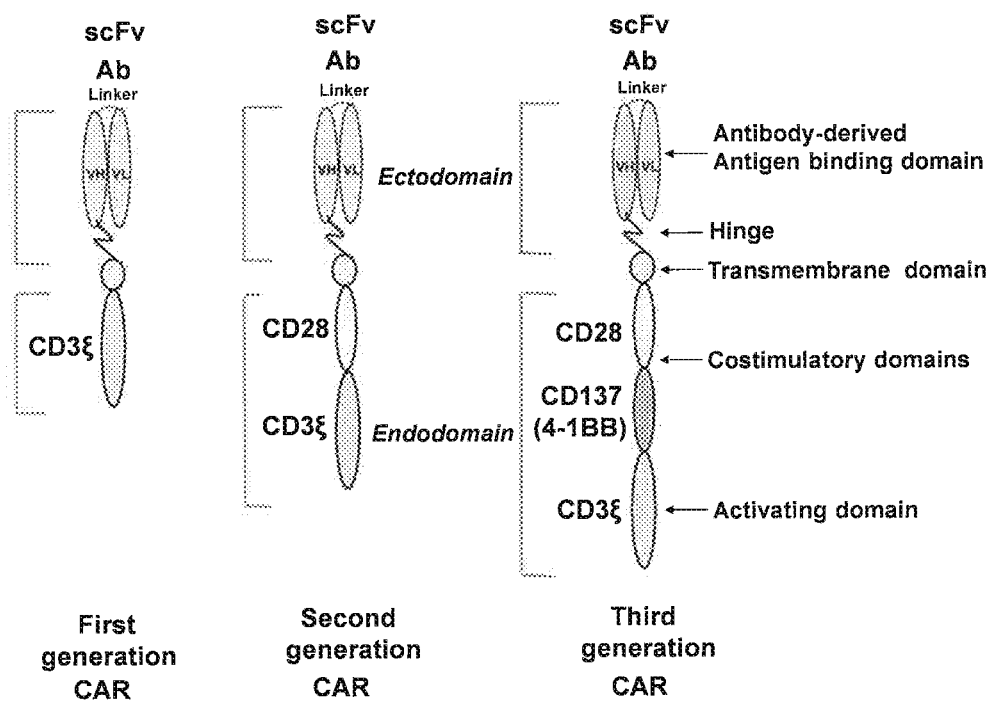
FIG. 1 shows the structure of CAR from first to third generation.

As used herein, "adoptive cell therapy" (ACT) is a treatment that uses a cancer patient's own T lymphocytes with anti-tumor activity, expanded in vitro and reinfused into the patient with cancer.

As used herein, "affinity" is the strength of binding of a single molecule to its ligand. Affinity is typically measured and reported by the equilibrium dissociation constant ($K_D$ or Kd), which is used to evaluate and rank order strengths of bimolecular interactions.

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, a FLAG-tag, or FLAG octapeptide, or FLAG epitope, is a polypeptide protein tag that can be added to a protein using recombinant DNA technology, having the sequence motif DYKDDDDK (SEQ ID NO: 1). It can be fused to the C-terminus or the N-terminus of a protein, or inserted within a protein.

As used herein, the term "humanized" generally refers to a process of making an antibody or immunoglobulin binding proteins and polypeptides derived from a non-human species (e.g., mouse or rat) to be less immunogenic to humans, while still retaining antigen-binding properties of the original antibody, using genetic engineering techniques. In some embodiments, the binding domain(s) of an antibody or an immunoglobulin binding protein or polypeptide (e.g., light and heavy chain variable regions, Fab, scFv) are humanized. Non-human binding domains can be humanized using techniques known as CDR grafting, including reshaping, hyperchimerization, and veneering. If derived from a non-human source, other regions of the antibody or immunoglobulin binding proteins and polypeptides, such as the hinge region and constant region domains, can also be humanized.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known to a person skilled in the art.

As used herein, a "tumor antigen" means a biological molecule having antigenecity, expression of which causes cancer.

Description

The present invention provides CD47-CAR and CD47-CAR-T cells that target CD47 tumor antigen which is highly overexpressed in many types of cancer such as ovarian, bladder, leukemia and lymphoma. The present invention designs CAR (chimeric antigen receptor)-T cells that bind to CD47 antigen. The invention uses ScFv (single chain variable fragment) from mouse CD47 antibody and humanized CD47 antibody to generate CD47-CAR-T cells for targeting different cancer cell lines. The CD47-CAR-T cells of the present invention have high cytotoxic activity against several cancer cells: pancreatic and ovarian cancer lines. The humanized scFv has an advantage in that it decreases potential immune response against mouse sequence in patients.

The present invention is directed to a chimeric antigen receptor (CAR) fusion protein comprising from N-terminus to C-terminus: (i) a single-chain variable fragment (scFv) comprising $V_H$ and $V_L$, wherein scFv has a high affinity against CD47, (ii) a transmembrane domain, (iii) a co-stimulatory domain of CD28, and (iv) an activating domain. The CAR may further comprise a second scFv in (i), wherein the second scFv is against another tumor antigen such as Epidermal growth factor receptor (EGFR); such CAR is referred to as a bispecific CAR.

Figure 2:
FIG. 2 shows the structures of CD47 CAR constructs.

The CAR construct (FIG. 2) contains CD8 signaling peptide, CD47 scFv, CD8 hinge, CD28 transmembrane domain, and CD3 zeta activation domains.

The CAR of the present invention comprises a single chain variable fragment (scFv) that binds specifically to human CD47. The heavy chain (H chain) and light chain (L chain) fragments of an anti-CD47 antibody are linked via a linker sequence. For example, a linker can be 5-20 amino acids. The scFv structure can be VL-linker-VH, or VH-linker-VL, from N-terminus to C-terminus.

The CAR of the present invention comprises a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor $\alpha$ or $\beta$ chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. In preferred embodiments, the transmembrane domain is derived from CD28 or CD8, which give good receptor stability.

In the present invention, the co-stimulatory domain is selected from the group consisting of human CD28, 4-1BB (CD137), ICOS-1, CD27, OX 40 (CD137), DAP10, and GITR (AITR).

The endodomain (the activating domain) is the signal-transmission portion of the CAR. After antigen recognition, receptors cluster and a signal is transmitted to the cell. The most commonly used endodomain component is that of CD3-zeta (CD3 Z or CD3ζ), which contains 3 ITAMs. This transmits an activation signal to the T cell after antigen is bound. CD3-zeta may not provide a fully competent activation signal and additional co-stimulatory signaling may be needed. For example, one or more co-stimulating domains can be used with CD3-Zeta to transmit a proliferative/survival signal.

The CAR fusion protein optionally comprises a FLAG tag located at N-terminus to scFv, or C-terminus to scFv, or between $V_H$ and $V_L$. The FLAG tag needs to be in extracellular domain, and not in the intracellular domain. In addition to FLAG tag, other tags may be used in the construct. FLAG tag is a preferred tag because it does not cause immunogenicity and has decreased level of cytokine secretion.

The CAR of the present invention may comprise a signal peptide N-terminal to the ScFv so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present invention may comprise a spacer sequence as a hinge to connect scFv with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells modified to express the chimeric antigen receptor fusion protein as described above. CAR-T cells of the present invention bind to a human CD47 via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index.

T cells modified to express the CAR can be used as a therapeutic agent for a disease. The therapeutic agent comprises the T cells expressing the CAR as an active ingredient, and may further comprise a suitable excipient. Examples of the excipient include pharmaceutically acceptable excipients known to a person skilled in the art.

The present invention demonstrates a high activity of CD47-CAR-T cells against cancer cell lines with a high expression of CD47. CD47-CAR-T cells of the present invention effectively killed ovarian, pancreatic and other cancer cells and produced high level of cytokines that correlated with expression of CD47 antigen. The present invention demonstrates that intra-tumor injection of CD47-CAR-T cells significantly decreased pancreatic BxPC3 xenograft tumor growth versus two controls: 1×PBS and CD24-CAR-T cells that were accompanied by increased human CD3 zeta IHC staining in CD47-CAR-T cell treated tumors versus control tumors.

The inventors have designed humanized CD47 ScFv that binds to human CD47 antigen by both ELISA and MC staining using human tumor samples. The humanized CD47 scFV has human frame sequences instead of mouse frame sequences flanking mouse CDR, and thus it decreases potential immune response against mouse ScFv. The humanized CD47 antibody has some mutations inside mouse CDR, which increases binding to CD47 antigen.

The humanized CD47-CAR-T cells of the present invention effectively killed cancer cell lines with a high expression of CD47 and did not kill and did not produce cytokines in CD47-negative cancer cells. Thus, mouse CD47-CAR-T cells and humanized CD47-CAR-T cells provides a cellular therapy for solid and hematological cancers.

This application shows a high specificity of CD47-CAR-T cells to CD47-positive cancer cells with a high expression of CD47 and an absence of CAR-T activity in target cells with low expression of CD47 such as Hela-CD19 cells. Thus, a therapeutic window exists where CD47-CAR-T cells affect only highly expressing CD-47 cells. In addition, CD47-CAR-T cells did not decrease mouse body weight, suggesting no toxic effect from CAR-T cells. Different approaches of CAR-T cell regulation such as switch-on, switch-off mechanisms; bi-specific CARs; regulation of cytokines involved in cytokine release syndrome and other approaches may be applied to increase safety and to overcome the major challenges of this CAR-T cell therapy.

Intra-tumor injection of CD47-CAR-T cells increases the safety of these cells. The majority of CD47-CAR-T cells are localized inside tumors and not in the blood. Thus, regional intra-tumor delivery of CD47-CAR-T cells is a feasible approach in clinic. Regional delivery of CD47-CAR-T cells may be advantageous for increased safety by direct delivery of CAR-T to tumors with less repressive effects of microenvironments and other mechanisms.

CD47 is also highly expressed in cancer stem cells, which are the most aggressive type of tumor cells. Thus, CD47-CAR-T cells can be used to target cancer stem cells. The present invention demonstrates an approach to target cancer cells with CD47-CAR-T cells. It demonstrates the high efficacy of CD47-CAR-T cells against cancer cells in vitro and in vivo and provides an anti-cancer cellular therapeutics.

Bispecific CD47- and another tumor antigen (EGFR, HER-2, VEGFR, etc.) CAR-T cells can be used for immunotherapy. The construct of the bispecific CAR-T cells contains a first scFv against CD47, and a second scFv against a second tumor antigen. CAR-T cells with bispecific antibodies can target cancer cells that overexpress two tumor antigens more effectively and specifically than CAR-T cells with one single antibody. Bispecific CAR-T cells can be advantageous when one tumor antigen becomes down-regulated, because the bispecific CAR-T cells can target the other tumor antigen. EGFR scFv is illustrated in Example 14 of the present application. HER-2 scFv is reported in Sadelain et al (J. Immunol. 2009, 183:5563-5574), VEGFR scFv is reported in Chinnasamy et al (J. Clin. Invest. 2010, 120 (11): 3953-3968); which are incorporated in reference in their entirety.

Combination of CD47-CAR-T with CAR-T targeting other tumor antigens or tumor microenvironment antigens (VEGFR-1-3) (dual CAR-T) can be used to enhance activity of monotherapy CD47-CAR.

CD47 CAR-T can be used in combination with different chemotherapy: checkpoint inhibitors; targeted therapies, small molecule inhibitors, and antibodies.

Tag-(FLAG tag or other tag) conjugated CD47 scFv can be used for CAR constructs.

Third generation CAR-T or other co-activation signaling domains can be used for the same CD47-scFv inside CAR.

CD47-CAR-T cells can be used to activate phagocytosis and block "don't eat" signaling.

The following examples further illustrate the present invention. These examples are intended merely to be illustrative of the present invention and are not to be construed as being limiting.

EXAMPLES

Materials and Methods

Example 1

Cell Lines

Hela cells were purchased from the ATCC (Manassas, Va.) and cultured in DMEM with 10% FBS and 1% penicillin/streptomycin. Hela-CD19 cells with stable expression of CD19 were maintained in DMEM with 10% FBS, puromycin and penicillin/streptomycin.as described in Berahovich, et al., Front. Biosci. (Landmark Ed.) 2017, 22, 1644-1654. Human peripheral blood mononuclear cells (PBMC) were isolated from whole blood obtained in the Stanford Hospital Blood Center (Stanford, Calif., USA) according to IRB-approved protocol using Ficoll-Paque solution (GE Healthcare, Chicago, Ill.). HEK293FT cells from AlStem (Richmond, Calif., USA) were cultured in DMEM containing 10% FBS and penicillin/streptomycin. SKOV-3 cell line was obtained from ATCC and cultured in RPMI plus 10% FBS and penicillin/streptomycin. Normal human keratinocytes were obtained from the Lonza company and cultured in keratinocyte medium (Lonza, Anaheim, Calif.) according to the manufacturer's protocol. BxPC3, PANC-1, A1847, A375, A549 and Hep-3 B were obtained from ATCC and cultured in DMEM with 10% FBS and penicillin/streptomycin. The cell lines were authenticated by flow cytometry in our laboratory, using cell-specific surface markers or by ATCC.

Example 2

CAR Constructs

CD47 ScFv from B6H12 antibody was inserted using Nhe I and Xho I s between CD8-alpha signaling peptide, and CD8-alpha hinge, with down-stream fused CD28 transmembrane domain, CD28 co-activation domain and CD3 activation domain. This CD47-CAR construct was flanked by Xba I and Eco R I sites in pCD510 lentiviral vector (Systems Bioscience, Palo Alto, Calif.). The same construct was done with humanized CD47 ScFv and Mock control ScFv of intracellular protein, called humanized CD47 and Mock-CAR, respectively. CD24 ScFv from Promab Biotechnologies (Richmond, Calif.) CD24 (clone 4F4E10) antibody was used as above for the CD24-CAR construct. The CAR were synthesized and sequenced in both directions by Syno Biological (Beijing, China).

Example 3

Generation of CAR-Encoding Lentivirus

The lentiviral CARs were used for generation of lentivirus using 293 FT cells, Lentivirus Packaging Mix and transfection agent (Alstem, Richmond, Calif.) as described in Berahovich, et al. The virus titers were determined by quantitative RT-PCR using the Lenti-X qRT-PCR kit (Takara Bio, Mountain View, Calif.) according to the manufacturer's protocol and the 7900HT thermal cycler (Thermo Fisher Scientific, South San Francisco, Calif.). The lentiviral titers were expressed in pfu/mL and ranged $1\text{-}10\times10^8$ pfu/mL.

Example 4

Generation and Expansion of CAR-T Cells

PBMC were suspended at $1\times10^6$ cells/mL in AIM V-AlbuMAX medium (Thermo Fisher) containing 10% FBS with 300 U/mL IL-2 (Thermo Fisher). PBMC were activated with an equal number of CD3/CD28 Dynabeads (Thermo Fisher), and cultured in non-treated 24-well plates. At 24 and 48 h, lentivirus was added to the cultures at a multiplicity of infection (MOI) of 5 with 1 µL of TransPlus transduction enhancer (AlStem). The CAR-T cells were counted every 2-3 days and fresh medium with 300 U/mL IL-2 was added to the cultures to maintain the cell density at $1\times10^6$ cells/mL.

Example 5

Flow Cytometry

To measure CAR expression, $5\times10^5$ cells were suspended in 100 µL of buffer (1×PBS with 0.5% BSA) and incubated on ice with 1 µL of human serum (Jackson Immunoresearch, West Grove, Pa., USA) for 10 min. Then 1 µL of allophycocyanin (APC)-labeled anti-CD3 (eBioscience, San Diego, Calif., USA), 2 µL of 7-aminoactinomycin D (7-AAD, BioLegend, San Diego, Calif., USA), and 2 µL of anti-F (ab)2 or its isotype control was added, and the cells were incubated on ice for 30 min. The cells were rinsed with buffer, and acquired on a FACSCalibur (BD Biosciences, San Jose, Calif.). Cells were analyzed first for light scatter versus 7-AAD staining, then the 7-AAD⁻ live gated cells were plotted for CD3 staining versus F(ab)2 staining or isotype control staining. In some experiments anti-F(ab)2 staining alone was done. For the mouse tumor studies, 100 µL of blood was stained at room temperature for 30 min with 1 µL of APC anti-CD3, 2 µL of fluorescein isothiocyanate (FITC)-labeled anti-CD8a (eBioscience), 2 µL of 7-AAD. Erythrocytes were lysed with 3.5 mL of RBC lysing solution (150 mM $NH_4Cl$, 10 mM $NaHCO_3$, 1 mM EDTA pH 8), then leukocytes were collected by centrifugation and rinsed with 2 mL of cold buffer before acquisition. For expression of CD47, mouse B6H12 antibody from (BioLegend) that was used according to the manufacturer's protocol at 10 m/mL concentration. For expression of CD24, mouse CD24 clone 4F4E10 (Promab Biotechnologies, Richmond, Calif., USA) was used at 10m/mL. The isotype IgG1 isotype antibody was used at 10 µg/mL from (BioLegend).

Example 6

Real-Time Cytotoxicity Assay (RTCA)

Adherent target cells were seeded into 96-well E-plates (Acea Biosciences, San Diego, Calif., USA) at $1\times10^4$ cells per well and monitored in culture overnight with the impedance-based real-time cell analysis (RTCA) iCELLigence system (Acea Biosciences). The next day, the medium was removed and replaced with AIM V-AlbuMAX medium containing 10% FBS±$1\times10^5$ effector cells (CAR-T cells or non-transduced T cells), in triplicate. The cells were monitored for another 2 days with the RTCA system, and impedance was plotted over time. Cytolysis was calculated as (impedance of target cells without effector cells—impedance of target cells with effector cells)×100/impedance of target cells without effector cells.

Example 7

Cytokine ELISA Assay

The target cells were cultured with the effector cells (CAR-T cells or non-transduced T cells) at a 1:1 ratio ($1\times10^4$ cells each) in U-bottom 96-well plates with 200 µL of AIM V-AlbuMAX medium containing 10% FBS, in triplicate. After 16 h the top 150 µL of medium was transferred to V-bottom 96-well plates and centrifuged at 300 g for 5 min to pellet any residual cells. In some experiments supernatant after RTCA assay at E:T=10:1 was used for cytokine ELISA assays. The supernatant was transferred to a new 96-well plate and analyzed by ELISA for human cytokine levels (IFN-gamma, IL-2, IL-6) using kits from Thermo Fisher (South San Francisco, Calif.) according to the manufacturer's protocol.

Example 8

Mouse Xenograft Tumor Growth

Six-week old male NSG mice (Jackson Laboratories, Bar Harbor, Me., USA) were housed and manipulated in strict accordance with the Institutional Animal Care and Use Committee (IACUC). Each mouse was injected subcutaneously with $2\times10^6$ BxPC3 cells in sterile 1×PBS and then CAR-T cells were injected intratumorally with three doses: $2\times10^5$ cells/mice; $2\times10^6$ cells/mice; $2.8\times10^6$ cells/mice doses at days 20, 27, and 34 respectively, and the xenograft tumor growth was analyzed. Tumor sizes were measured with calipers twice-weekly and tumor volume (in $mm^3$) was determined using the formula $W^2L/2$, where W is tumor width and L is tumor length. Tumors were excised and fixed in 4% paraformaldehyde, then embedded in paraffin wax and stained by immunohistochemistry. At the end of the intravenous CAR-T cell study, 100 µL of blood was collected and stained with different antibodies by flow cytometry as indicated above.

Example 9

Immunohistochemistry (IHC) Staining

Tumor tissue sections (4 µm) were incubated in xylenes twice for 10 min, then hydrated in graded alcohols and rinsed in 1×PBS. Antigen retrieval was performed for 20 min in a pressure cooker using 10 mM citrate buffer, pH 6.0. The sections were cooled, rinsed with PBS, incubated in a 3% H₂O₂ solution for 10 min, and then rinsed with 1×PBS. The tissue sections were incubated in goat serum for 20 min and then incubated with rabbit anti-cleaved caspase-3 (Asp175, Cell Signaling Technology, Danvers, Mass., USA) or rabbit IgG (Jackson Immunoresearch, West Grove, Pa., USA) at 0.2 μg/mL overnight at 4° C. The sections were rinsed with PBS, incubated with biotin-conjugated goat anti-rabbit IgG for 10 min, rinsed with PBS, incubated with streptavidin-conjugated peroxidase for 10 min, and rinsed with PBS. Finally, the sections were incubated in DAB substrate solution for 2-5 min, immersed in tap water, counterstained with hematoxylin, rinsed with water, and dehydrated in graded alcohols and xylenes. Coverslips were mounted with glycerin. Images were acquired on a DMB5-2231PL microscope (Motic, Xiamen, China) with Images Plus 2.0. software.

Example 10

Humanization of CD47 Antibody

The mouse B6H12 CDR was used for humanization using IgBLAST (NCBI) software according to the methods described in Almagro, et al. (Front. Biosci., 2008, 13, 1619-1633). The human frames of human clones with the highest homology were used for humanized pairs. Mouse CDR were inserted into these clones and four different variants were generated for testing by ELISA.

Example 11

Binding Assay with Humanized and Mouse CD47 scFv

The mouse or humanized CD47 ScFv contained VL and VH sequences that were linked with G4Sx3 linker. The ScFvs were fused in frame with C-terminal human Fc inside pYD11 vector used for recombinant CD47 ScFv protein expression. The supernatant with mammalian expressed ScFv protein were used for binding assay at equal amount. All ScFv were checked by Western blotting with anti-human Fc antibody for expression. The human extracellular domain (19-41 amino-acids) of human CD47 protein (Gen Bank ID: NM_001777.3) was fused with mouse Fc and used for ELISA assay with CD47 ScFv. The OD reading at 450 nm was used for detecting binding. The in silico model was generated for humanized VH and VL sequences based on the mouse sequences.

Results

Statistical Analysis

Data were analyzed and plotted with Prism software (GraphPad, San Diego, Calif.). Comparisons between two groups were performed by unpaired Student's t test, and comparisons between three groups were performed by one-way ANOVA with Tukey's post-hoc test, except where noted. The difference was considered significant with p-value<0.05.

Example 12

Mouse CD47 ScFv CAR Construct Sequence

The amino acid sequences of all segments of CD47 CAR constructs used in our experiments are shown below. Each segment can be replaced with an amino acid sequence having at least 95% identity.

```
<Human CD8 Signal peptide>
                             SEQ ID NO: 2
        MALPVTALLLPLALLLHAARP
```

<Nhe I site> This site is optional for cutting out scFv if desired, and can be replaced by other restriction enzyme site.
AS
Mouse anti-CD47 scFv (VH-Linker-VL)

```
<VH>
                             SEQ ID NO: 3
EVQLVESGGDLVKPGGSLKLSCAASGFTFSGYGMSWVRQTPD
KRLEWVATITSGGTYTYYPDSVKGRFTISRDNAKNTLYLQIDS
LKSEDTAIYFCARSLAGNAMDYWGQGTSVTVSS

<linker>
                             SEQ ID NO: 4
GGGGSGGGGSGGGGS

<VL>
                             SEQ ID NO: 5
DIVMTQSPATLSVTPGDRVSLSCRASQTISDYLHWYQQKSHES
PRLLIKFASQSISGIPSRFSGSGSGSDFTLSINSVEPEDVGVYYC
QNGHGFPRTFGGGTKLEIK
```

<Xho I site> This site is optional for cutting out scFv if desired, and can be replaced by other restriction enzyme site.
LE

```
<CD8 hinge>
                             SEQ ID NO: 6
KPTTTPAPRPPTPAPTIASQPLSLRPEASRPAAGGAVHTRGLDF
ASDKP <Transmembrane Domain TM28>
                             SEQ ID NO: 7
FWVLVVVGGVLACYSLLVTVAFIIFWV <Co-stimulating domain CD28>
                             SEQ ID NO: 8
RSKRSRLLHSDYMNMTPRRPGPTRKHYQPYAPPRDFAAYRS <Activation domain CD3-zeta>
                             SEQ ID NO: 9
RVKFSRSADAPAYQQGQNQLYNELNLGRREEYDVLDKRRGRD
PEMGGKPRRKNPQEGLYNELQKDKMAEAYSEIGMKGERRRGK
GHDGLYQGLSTATKDTYDALHMQALPPR Mouse CD47 ScFv CAR sequence can be shown as
                             SEQ ID NO: 10:
MALPVTALLLPLALLLHAARPASEVQLVESGGDLVKPGGSLKL

SCAASGFTFSGYGMSWVRQTPDKRLEWVATITSGGTYTYYPD

SVKGRFTISRDNAKNTLYLQIDSLKSEDTAIYFCARSLAGNAM

DYWGQGTSVTVSSGGGGSGGGGSGGGGSDIVMTQSPATLSVT

PGDRVSLSCRASQTISDYLHWYQQKSHESPRLLIKFASQSISGIP

SRFSGSGSGSDFTLSINSVEPEDVGVYYCQNGHGFPRTFGGGT

KLEIKLEKPTTTPAPRPPTPAPTIASQPLSLRPEASRPAAGGAVH

TRGLDFASDKPFWVLVVVGGVLACYSLLVTVAFIIFWVRSKRS
```

```
RLLHSDYMNMTPRRPGPTRKHYQPYAPPRDFAAYRSRVKFSRS

ADAPAYQQGQNQLYNELNLGRREEYDVLDKRRGRDPEMGGKP

QRRKNPQEGLYNELQKDKMAEAYSEIGMKGERRRGKGHDGLY

QGLSTATKDTYDALHMQALPPR
```

A "mock" CAR with an scFv specific for an intracellular protein—and thus not reactive with intact cells—can be constructed in the same manner.

Example 13

Humanized CD47 ScFv CAR Construct Sequence

The bioinformatics approach was performed to humanize VH and VL of the mouse CD47 antibody B6H12 according to the method described by Almagro, et al., Front. Biosci. 2008, 13, 1619-1633; and Gilliland, et al., Methods Mol. Biol., 2012, 841, 321-349.

The amino acid sequence of all segments of humanized CD47 ScFv CAR construct used in our experiments are the same as those shown in Example 12, except the scFv of mouse anti-CD47 sequence is replaced with a humanized anti-CD47 sequence as shown below. Each segment can be replaced with an amino acid sequence having at least 95% sequence identity.

```
Humanized anti-CD47 scFv (VH-Linker-VL)
<VH>
                                       SEQ ID NO: 11
EVQLVESGGGLVQPGGSLRLSCAASGFTFSGYGMSWVRQAPGKGLEWVAT
ITSGGTYTYYPDSVKGRFTISRDNAKNSLYLQMNSLRAEDTAVYYCARSL
AGNAMDYWGQGTLVTVSS <linker>
                                        SEQ ID NO: 4
GGGGSGGGGSGGGGS <VL>
                                       SEQ ID NO: 12
EIVLTQSPATLSLSPGERATLSCRASQSISDYLHWYQQKPGQAPRLLIYF
ASQRATGIPARFSGSGSGTDFTLTISSLEPEDFAVYYCQQGHGFPRTFGG
GTKVEIK Humanized CD47 scFv is shown as SEQ ID No: 13:
EVQLVESGGGLVQPGGSLRLSCAASGFTFSGYGMSWVRQAPG

KGLEWVATITSGGTYTYYPDSVKGRFTISRDNAKNSLYLQMNS

LRAEDTAVYYCARSLAGNAMDYWGQGTLVTVSSGGGGSGGG

GSGGGGSEIVLTQSPATLSLSPGERATLSCRASQSISDYLHWYQ

QKPGQAPRLLIYFASQRATGIPARFSGSGSGTDFTLTISSLEPED

FAVYYCQQGHGFPRTFGGGTKVEIK

Humanized CD47 ScFv CAR can be shown as SEQ ID
NO: 14:
MALPVTALLLPLALLLHAARPASEVQLVESGGGLVQPGGSLRL

SCAASGFTFSGYGMSWVRQAPGKGLEWVATITSGGTYTYYPD

SVKGRFTISRDNAKNSLYLQMNSLRAEDTAVYYCARSLAGNA

MDYWGQGTLVTVSSGGGGSGGGGSGGGGSEIVLTQSPATLSLS

PGERATLSCRASQSISDYLHWYQQKPGQAPRLLIYFASQRATGI

PARFSGSGSGTDFTLTISSLEPEDFAVYYCQQGHGFPRTFGGGT

KVEIKLEKPTTTPAPRPPTPAPTIASQPLSLRPEASRPAAGGAV
```

```
HTRGLDFASDKPFWVLVVVGGVLACYSLLVTVAFIIFWVRSKR

SRLLHSDYMNMTPRRPGPTRKHYQPYAPPRDFAAYRSRVKFSR

SADAPAYQQGQNQLYNELNLGRREEYDVLDKRRGRDPEMGGK

PQRRKNPQEGLYNELQKDKMAEAYSEIGMKGERRRGKGHDGL

YQGLSTATKDTYDALHMQALPPR
```

Example 14

Bispecific EGFR-Flag-CD47-CD28-CD3 CAR Construct

The amino acid sequences of each segment of EGFR-Flag-CD47 ScFv CAR construct used in our experiments are the same as those shown in Example 12, except the scFv of EGFR, FLAG, and linker sequences are added at the N-terminal end of mouse anti-CD47 sequence as shown below. Each segment can be replaced with an amino acid sequence having at least 95% sequence identity.

```
Human anti-EGFR scFv (VH-Linker-VL-FLAG-Linker)
<VH>
                                       SEQ ID NO: 15
EVQLVQSGAEVKKPGSSVKVSCKASGGTFSSYAISWVRQAPGQ
GLEWMGGIIPIFGTANYAQKFQGRVTITADESTSTAYMELSSLR
SEDTAVYYCAREEGPYCSSTSCYGAFDIWGQGTLVTVSS <linker>
                                        SEQ ID NO: 4
GGGGSGGGGSGGGGS <VL>
                                       SEQ ID NO: 16
QSVLTQDPAVSVALGQTVKITCQGDSLRSYFASWYQQKPGQA
PTLVMYARNDRPAGVPDRFSGSKSGTSASLAISGLQSEDEADY
YCAAWDDSLNGYLFGAGTKLTVL <FLAG>
                                        SEQ ID NO: 1
FLAG tag is optional, for the purpose of detecting
expression., <linker>
                                        SEQ ID NO: 4

Bispecific EGFR-CD47 ScFv CAR sequence can be
shown as SEQ ID NO: 17:
MALPVTALLLPLALLLHAARPASEVQLVQSGAEVKKPGSSVKV
SCKASGGTFSSYAISWVRQAPGQGLEWMGGIIPIFGTANYAQK
FQGRVTITADESTSTAYMELSSLRSEDTAVYYCAREEGPYCSST
SCYGAFDIWGQGTLVTVSSGGGGSGGGGSGGGGSQSVLTQDP
AVSVALGQTVKITCQGDSLRSYFASWYQQKPGQAPTLVMYAR
NDRPAGVPDRFSGSKSGTSASLAISGLQSEDEADYYCAAWDDS
LNGYLFGAGTKLTVLDYKDDDDKGGGGSGGGGSGGGGSDIVM
TQSPATLSVTPGDRVSLSCRASQTISDYLHWYQQKSHESPRLLI
KFASQSISGIPSRFSGSGSGSDFTLSINSVEPEDVGVYYCQNGH
GFPRTFGGGTKLEIKGGGGSGGGGSGGGGSEVQLVESGGDLVK
PGGSLKLSCAASGFTFSGYGMSWVRQTPDKRLEWVATITSGGT
YTYYPDSVKGRFTISRDNAKNTLYLQIDSLKSEDTAIYFCARSL
AGNAMDYWGQGTSVTVSSLEKPTTTPAPRPPTPAPTIASQPLS
LRPEASRPAAGGAVHTRGLDFASDKPFWVLVVVGGVLACYSL
LVTVAFIIFWVRSKSRSLLHSDYMNMTPRRPGPTRKHYQPYAP
PRDFAAYRSRVKFSRSADAPAYQQGQNQLYNELNLGRREEYD
VLDKRRGRDPEMGGKPQRRKNPQEGLYNELQKDKMAEAYSEI
GMKGERRRGKGHDGLYQGLSTATKDTYDALHMQALPPR
```

Example 15

Mouse CD47-CAR-T Cells Kill CD47-Positive Cancer Cells

Figure 3A:
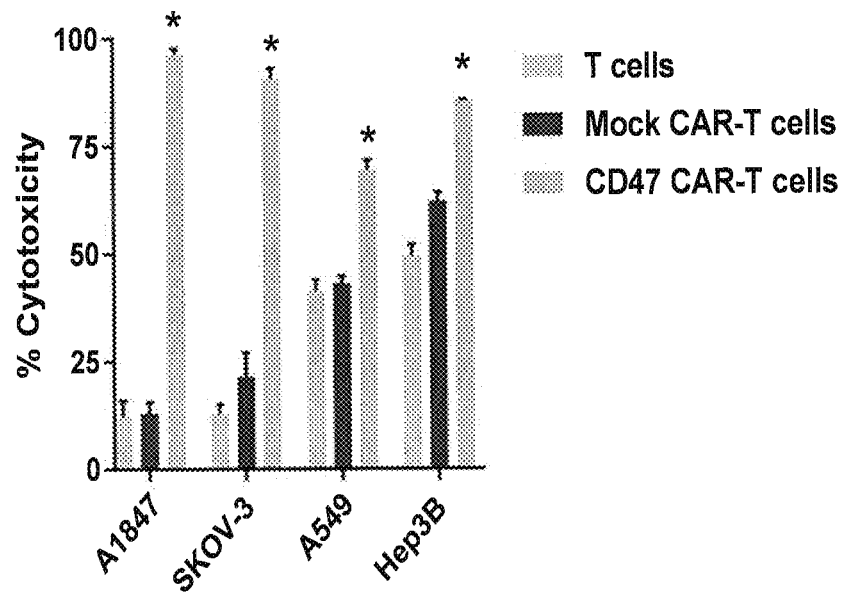
FIG. 3A shows cytotoxicity of CD47-CAR-T cells versus T cells and Mock-CAR-T cells. The quantitation of RTCA from three independent experiments is shown. * p<0.0001 CD47-CAR-T cells versus T cells and Mock CAR-T cells by 2-way ANOVA with Tukey's post-test.

The CD47 ScFv was used to generate second generation CAR-T cells, CD47-CAR-T cells with CD28 co-stimulatory domain and CD zeta activation domain (FIG. 2B). The CD47-CAR-T cells expanded >150-fold on day 14 in vitro and expressed CAR as demonstrated by FACS with F(ab)2 antibody. To test the killing activity in vitro, we tested CD47 CAR-T cells by RTCA assay (Real-time cytotoxicity assay) with CD47-positive cells expressing a high level of CD47 antigen: ovarian cancer cells, A1847, and SKOV-3 and with cancer cells expressing a low level of CD47: A549 cells and Hep3B cells. The CD47-CAR-T cells effectively killed high-expressing cancer cell lines such as A1847, SKOV-3, and CAR-T cells killed much less A549 and Hep3B and cells with a lower level of CD47 versus T cells or Mock-CAR-T cells. The cytotoxicity of cancer cells was significantly higher than T cells and Mock-CAR-T cells, p<0.0001 (FIG. 3A). This demonstrates CD47-dependent activity of CD47-CAR-T cells depending on expression of CD47 antigen.

Figure 3B:
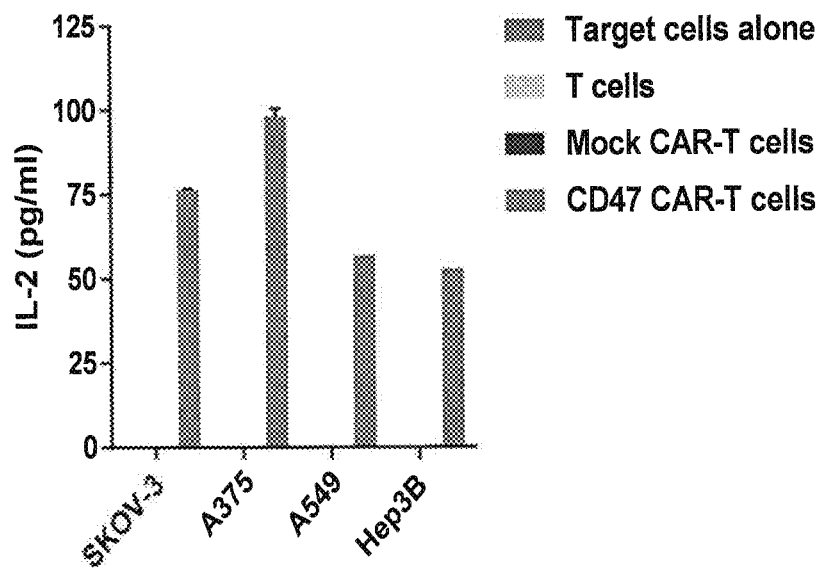
FIG. 3B shows CD47-CAR-T cells produce IL-2 in a CD47-dependent manner; high in CD47-positive cells and lower in CD47-negative cells. The Effector to target E:T ratio was 1:1. The bars show average IL-2 secretion by CD47 CAR-T cells from two independent experiments. * p<0.05, Student's t-test in SKOV-3 and A375 cells versus T cells, Mock CAR-T cells, A549 cells and Hep 3B cells.

The CD47-CAR-T cells produced 11-2 cytokine against cancer cells that was significantly higher in SKOV3 cells, highly positive for CD47 than in A549 and Hep3B cells with lower expression of CD47 (FIG. 3B). Thus, CD-47-CAR-T cells kill and secrete IL-2 cytokine in a CD47-dependent manner based on CD47 expression on the surface of cancer cells that is consistent with cytotoxicity data.

Example 16

Figure 4A:
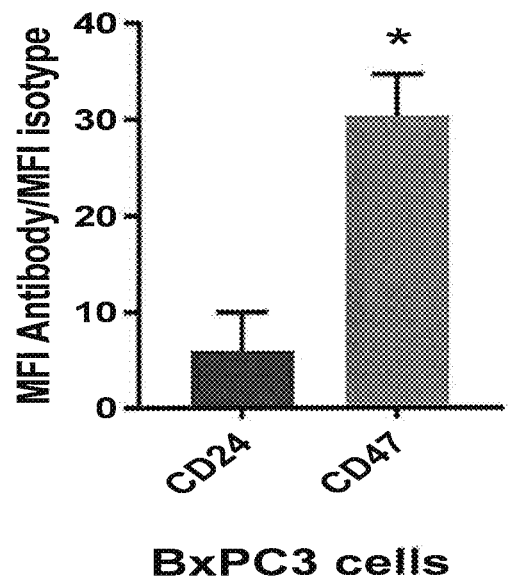
FIG. 4A shows CD47 expression is significantly higher than CD24 expression in BxPC3 pancreatic cancer cells. The bars show average ratio of MFI to isotype control IgG1 of CD24 and CD47 expression in BxPC3 cells±standard errors from two independent experiments. * p=0.029.
Figure 4B:
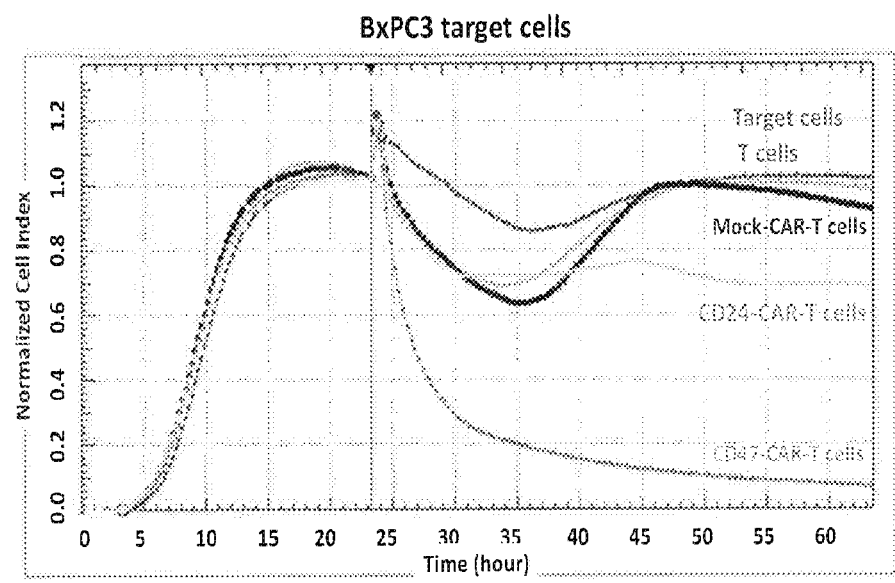
FIG. 4B shows CD47-CAR-T cells effectively killed BxPC3 cancer cell lines by RTCA assay.

CD47-CAR-T Cells Significantly Decrease BxPC3 Pancreatic Cancer Xenograft Tumor Growth To test in vivo efficacy of CD47-CAR-T cells, we used BxPC3 pancreatic cancer cells. We compared CD47-CAR-T cytotoxicity with Mock CAR-T control cells and CD24-CAR-T cells. FIGS. 4A-4G show CD47-CAR-T cells significantly decrease BxPC3 pancreatic cancer xenograft tumor growth. CD24-CAR-T cells with CD24-CAR ScFv were used as non-CD47 control CAR-T cells based on significantly lower expression of CD24 in BxPC3 cells compared to CD47 (FIG. 4A). The CD47-CAR-T cells expressed high cytotoxic activity against BxPC3 cells compared with Mock control CAR-T cells and CD24-CAR-T cells (FIG. 4B).

Figure 4C:
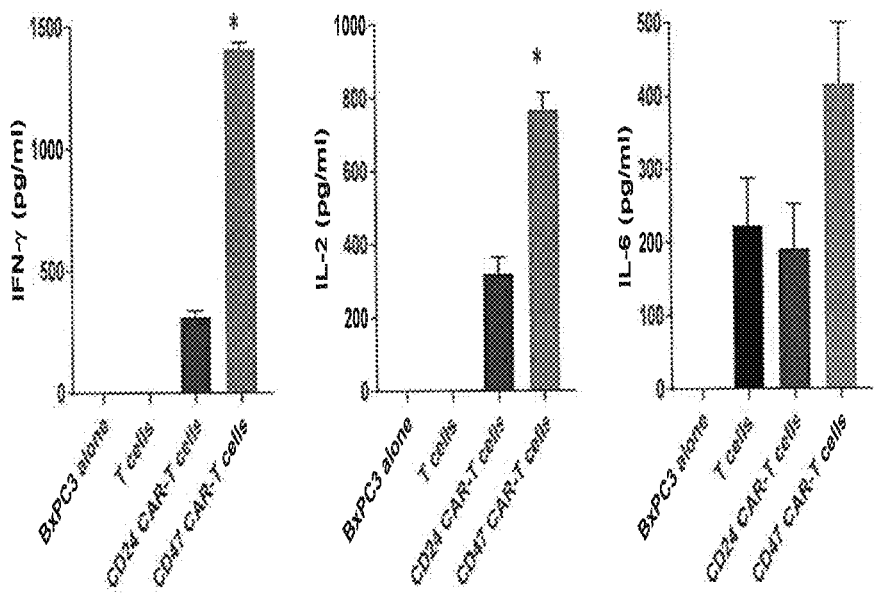
FIG. 4C shows CD47-CAR-T cells secreted high levels of cytokines: IFN-gamma, IL-2 and IL-6 against BxPC3 cells in vitro that was consistent with high cytotoxic activity of CD47-CAR-T cells against BxPCR3 cells shown in FIG. 4B. The supernatants from RTCA assay were used for cytokine ILISA assay. E:T=10:1. * p<0.05.
Figure 4D:
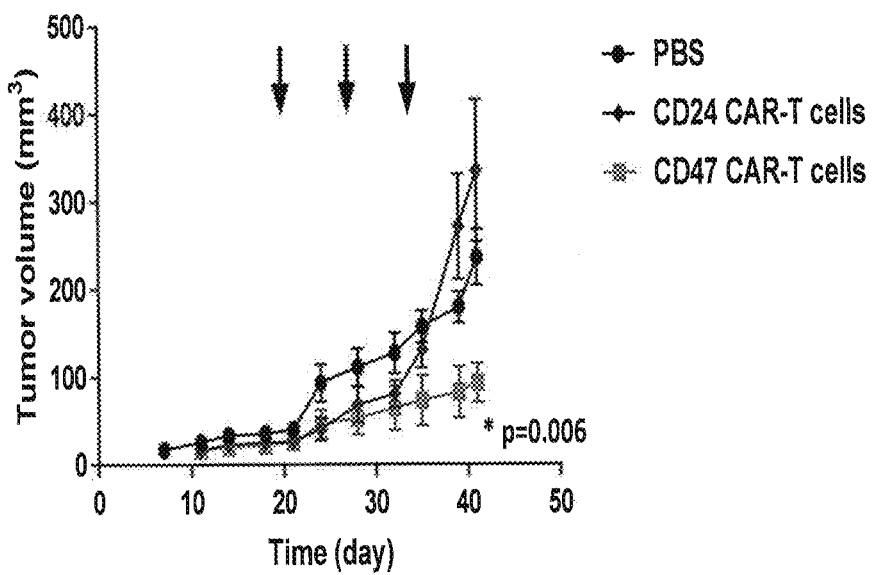
FIG. 4D shows CD47-CAR-T cells significantly decreased BxPC3 tumor growth, * p=0.006, CD47-CAR-T cells versus 1×PBS control. n=4-5 mice, CD47/CD24-CAR-T cells and 1×PBS groups, respectively.
Figure 4E:
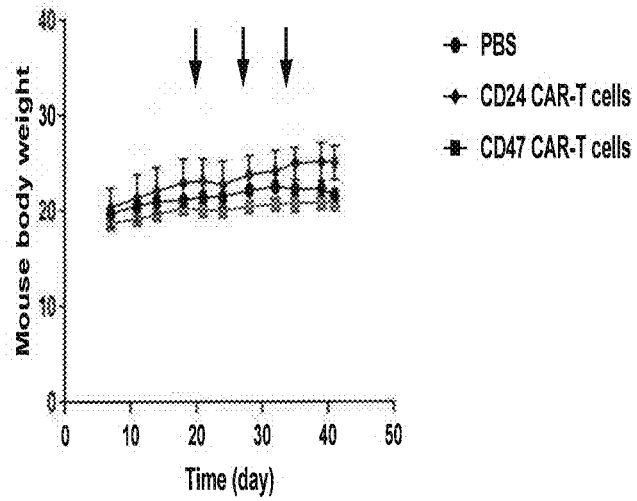
FIG. 4E shows CAR-T cells did not affect mice weight in CD47-CAR-T cell, CD24-CAR-T cell and 1×PBS control groups. Mice weight was measured in grams two times a week.
Figure 4F:
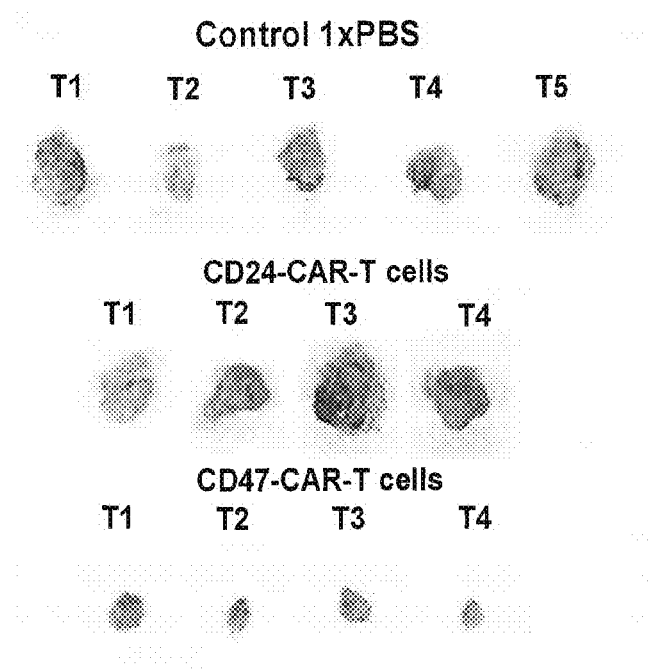

In addition, CD47-CAR-T cells expressed a significantly higher level of cytokines: IFN-gamma, IL-2 versus Mock and CD24-CAR-T cells (FIG. 4C), and expressed a high level of IL-6 against target BxPC3 cells versus Mock Control and CD24-CAR-T cells (FIG. 4C). We injected BxPC3 cancer cells subcutaneously into NSG mice to generate established xenograft tumors (FIG. 4D). Then three injections of CD47-CAR-T cells, control 1×PBS and CD24-CAR-T cells were applied intra-tumorally at days 20, 27 and 34. CD47-CAR-T cells significantly decreased BxPC3 xenograft tumor growth compared with controls, p <0.05 (FIG. 4D). CD47-CAR-T cells did not affect mice weight (FIG. 4E). The tumor size (FIG. 4F) and weight (FIG. 4G) from the CD47-CAR-T cell-treated group were significantly less (p<0.05) than from the control lx PBS and CD24-CAR-T cell groups.

Example 17

Humanized CD47 ScFv Effectively Binds CD47 Antigen and Detects CD47 in Tumor Samples A humanized version of CD 47 ScFv with a high affinity to the CD47 antigen is shown in FIG. 5A. The humanized VH and mouse B6H12 VH have the same CDR 1, 2, 3 regions of (CDRs regions are in italic and underlined). The humanized VH and mouse B6H12 VH have similar human frame regions, with differences in frame regions in larger font underlined. (FIG. 5A)

As to VL, the humanized version of CD47 antibody had three amino-acid changes in CDR2 and one amino acid changes in CDR3 region in VL versus mouse B6H12 (CDRs are all underlined and in italics, changes in CDR are shown in larger font and bold; CDR3 region is important for binding with antigen) (FIG. 5A).

Figure 5B:
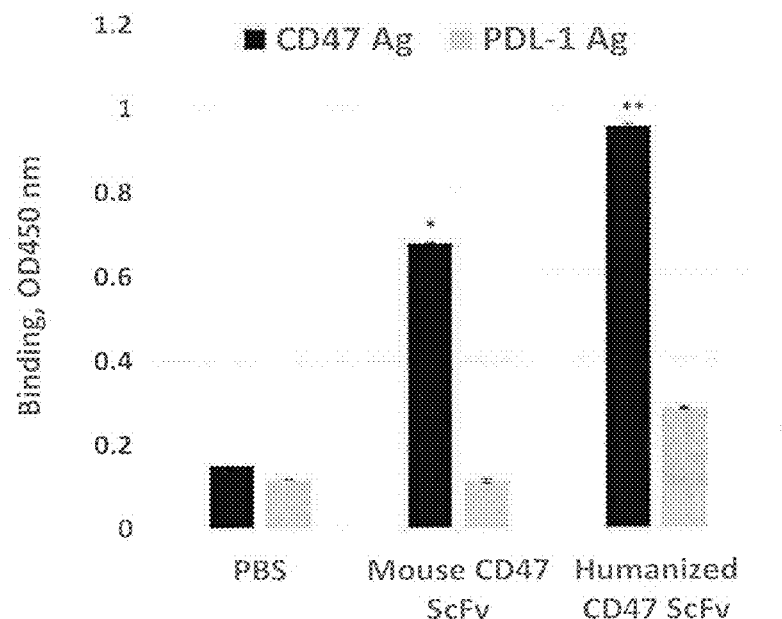
FIG. 5B shows an ELISA demonstrating high binding activity of humanized CD47 ScFv with CD47 antigen. Human PDL-1 antigen is a negative control. The binding activity was significantly higher than mouse CD47 ScFv. The bars show average of binding activity from two independent experiments. * p=0.0025, mouse CD47 versus PDL-1 control; ** p=0.0025 humanized CD47 vs. PDL-1 control; and p=0.0028 humanized CD47 vs. mouse CD47.
Figure 5C:
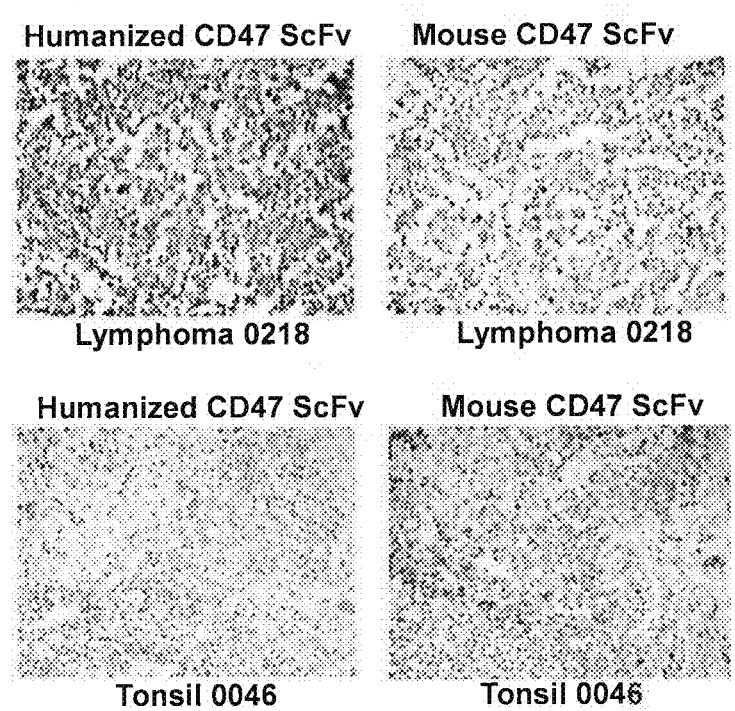
FIG. 5C shows IHC staining with humanized CD47 ScFv and mouse CD47 ScFv of tumor and normal samples. Similar staining is observed. MC with humanized CD47 ScFv demonstrates high staining in tumor samples and low staining in normal tissues.

We tested binding of humanized CD47 ScFv by ELISA (FIG. 5B). It had significantly higher binding than mouse CD47 ScFv and had higher binding than negative control PDL-1 (FIG. 5B). The humanized CD47 ScFv detected CD47 antigen better in lymphoma samples and similarly in other tumor samples (ovarian, gastric cancer (not shown) and less or similarly in normal such as tonsils (FIG. 5C).

Example 18

Figure 6A:
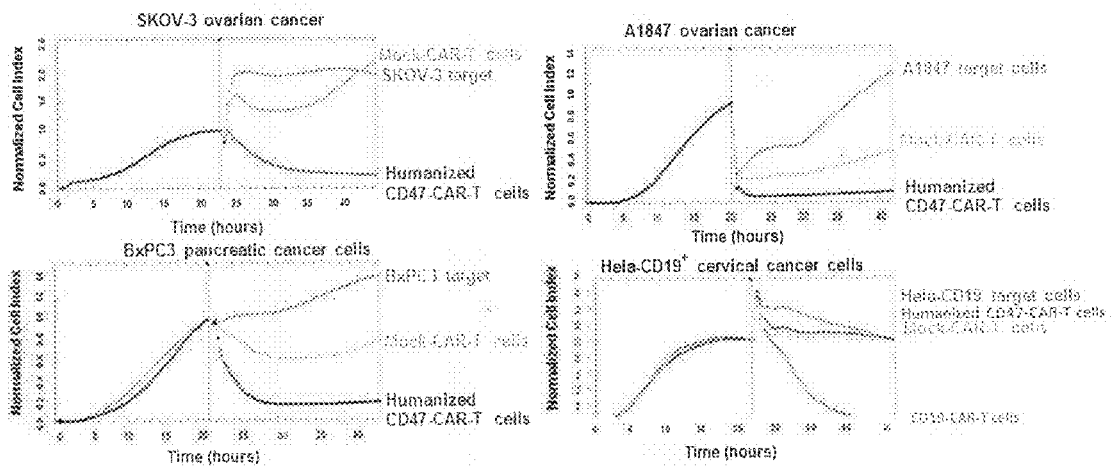
FIG. 6A shows an RTCA cytotoxicity assay with humanized CD47-CAR-T cells and CD47-positive or CD47-negative Hela-CD19 cancer target cells. CD47-CAR-T cells cytotoxic against CD47-positive but not against CD47-negative Hela-CD19 cells. Positive control CD19-CAR-T cells effectively kill CD19-positive Hela-CD19 cells.
Figure 6B:
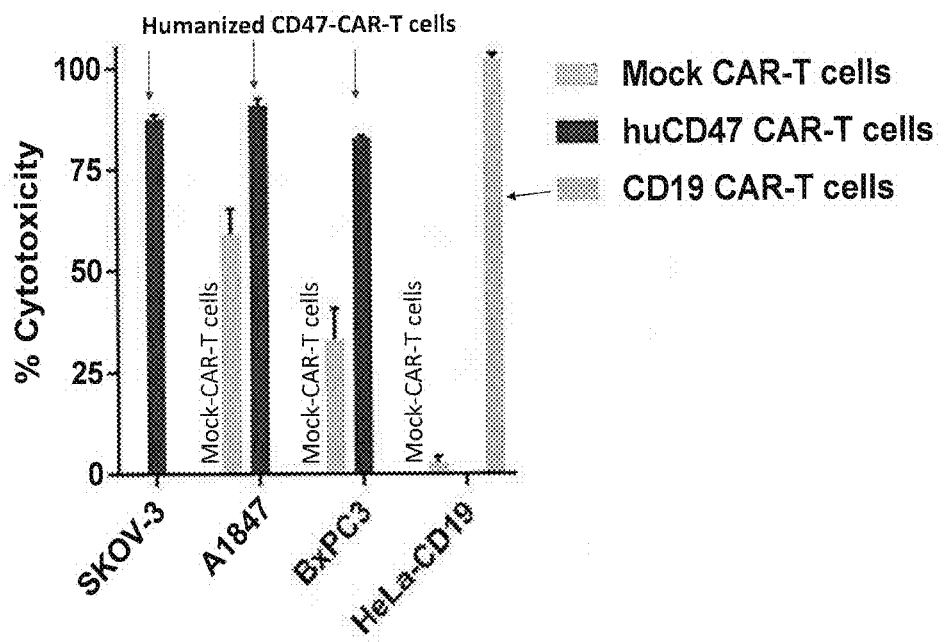
FIG. 6B illustrates the quantification of RTCA assay results, which show significantly increased CD47-CAR-T cell cytotoxicity with CD47-positive cancer cell lines but not with CD47-negative Hela-CD19 cells. * p<0.001, CD47-CAR-T cells versus Mock-CAR-T cells.
Figure 6C:
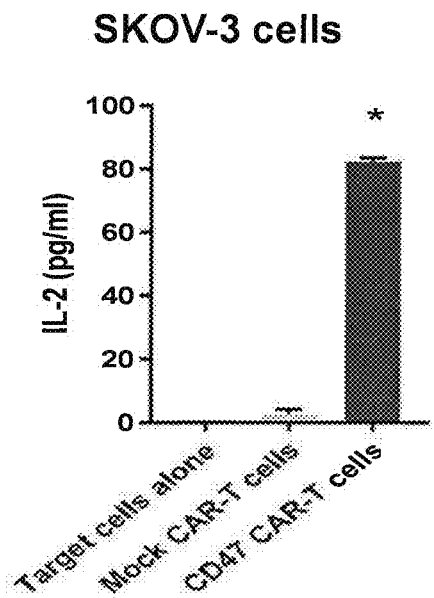
FIG. 6C shows secretion of IL-2 by humanized CD47-CAR-T cells with CD47-positive cells SKOV-3 cells. E:T ratio=1:1. p<0.05, CD47-CAR-T cells versus controls, n=3.
Figure 6D:
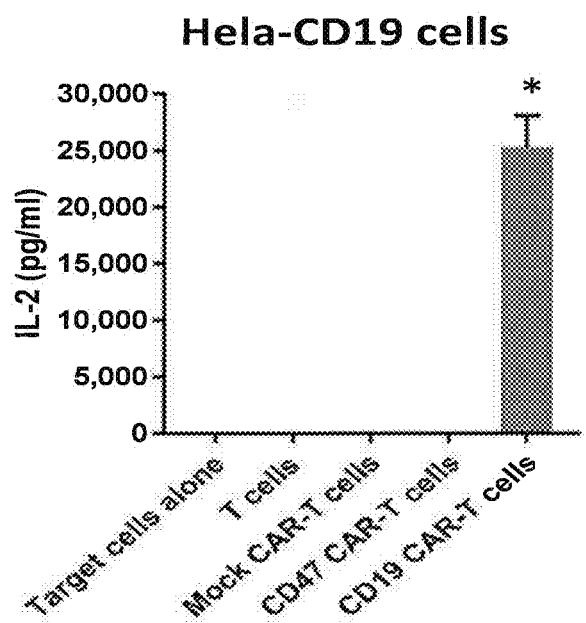
FIG. 6D shows that IL-2 is not secreted by CD47-CAR-T cells with CD47-negative cells, Hela-CD19 cells. Mock-CAR-T cells are negative control cells. CD19-CAR-T cells are positive control cells against Hela-CD19 target cells. E:T ratio=10:1. p<0.05, CD19-CAR-T cells versus controls, n=3.

Humanized CD47-CAR-T Cells Effectively Kill Cancer Cells in a CD47Dependent Manner We tested humanized CD47-CAR T cells against CD47 high-expressing ovarian: SKOV-3, A1847 and pancreatic, BxPC3 cancer cell lines, and low-expressing Hela-CD19 cancer cell line (FIG. 6A). Humanized CD47-CAR-T cells effectively killed CD47-positive cancer cells and had no killing activity against Hela-CD19 cancer cells with very low expression of CD47, while positive control CD19-CAR-T cells effectively killed Hela-CD19 cells (FIG. 6A, lower right panel). The CD47-CAR-T cytotoxicity was significantly increased in CD47-positive cells versus CD47-negative cells and control Mock CAR-T cells (p<0.05) (FIG. 6B). The IL-2 cytokine level secreted by CD47-CAR-T cells was also increased significantly (p<0.05) in SKOV-3-CD47-positive cell line versus Mock-CAR-T cells (FIG. 6C), but was not present in Hela-CD19 cells, negative for CD47 (FIG. 6D). In contrast, control CD19-CAR-T cells produced significantly (p<0.05) increased level of IL-2 in Hela-CD19-positive cells versus Mock-CAR-T cells (FIG. 6D). Thus, humanized CD47-CAR-T cells effectively and specifically killed cancer cell lines and produced cytokines in a CD47-dependent manner.

Example 19

Bi-specific EGFR-CD47CAR-T Cells Kill Cancer Cells

We generated bi-specific CAR by linking EGFR (C10) human antibody scFv-FLAG with CD47 scFv using G4Sx3 linker. (see Example 14).

Figure 7:
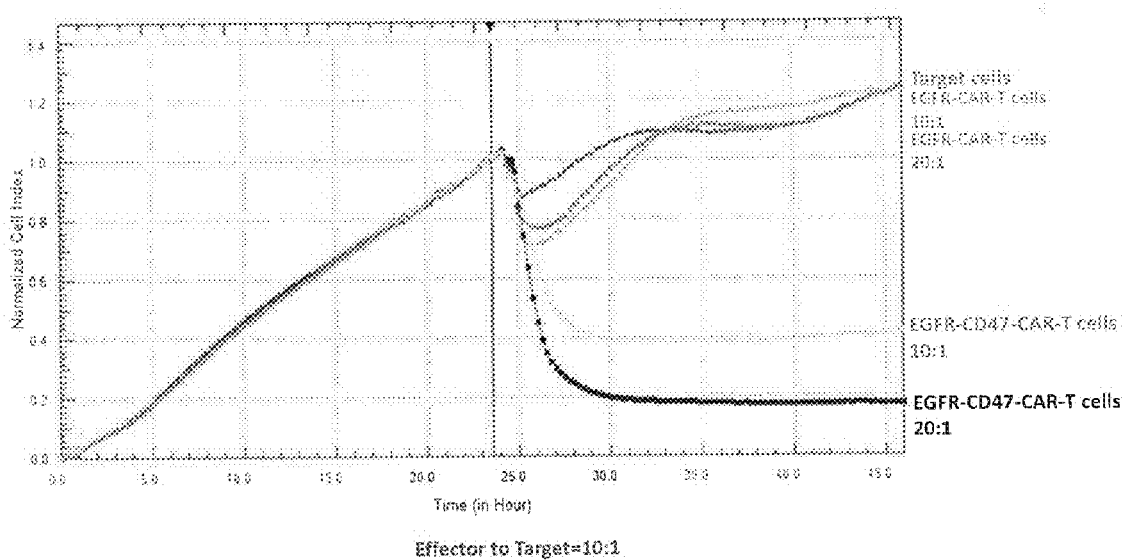
FIG. 7 shows bi-specific EGFR-CD47 CAR-T cells killed EGFR-negative MCF-7
Figure 8A:
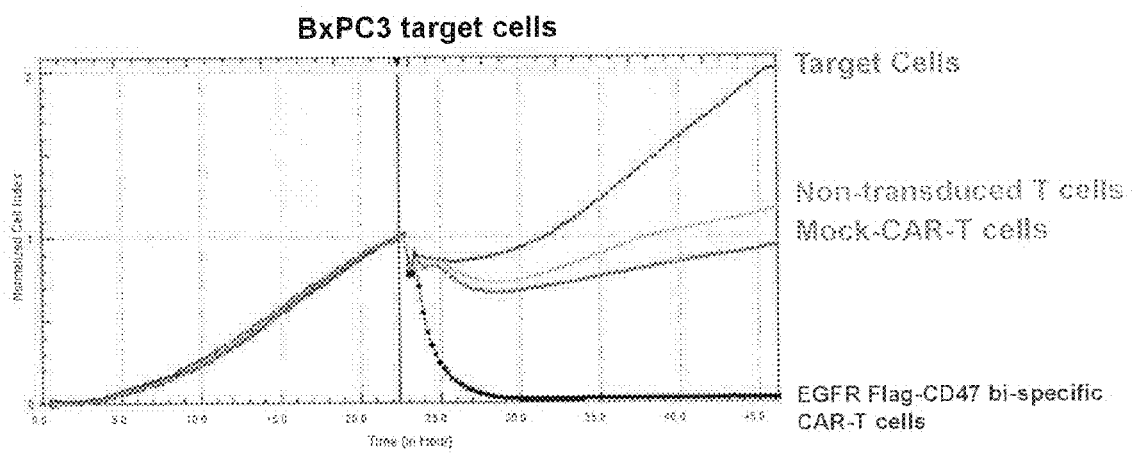
FIGS. 8A and 8B show bi-specific EGFR-CD47 CAR-T cells effective killed EGFR-positive and CD47-positive BxPC3 pancreatic cancer cells (FIG. 8A) and SKOV ovarian cancer cells (FIG. 8B).
Figure 8B:
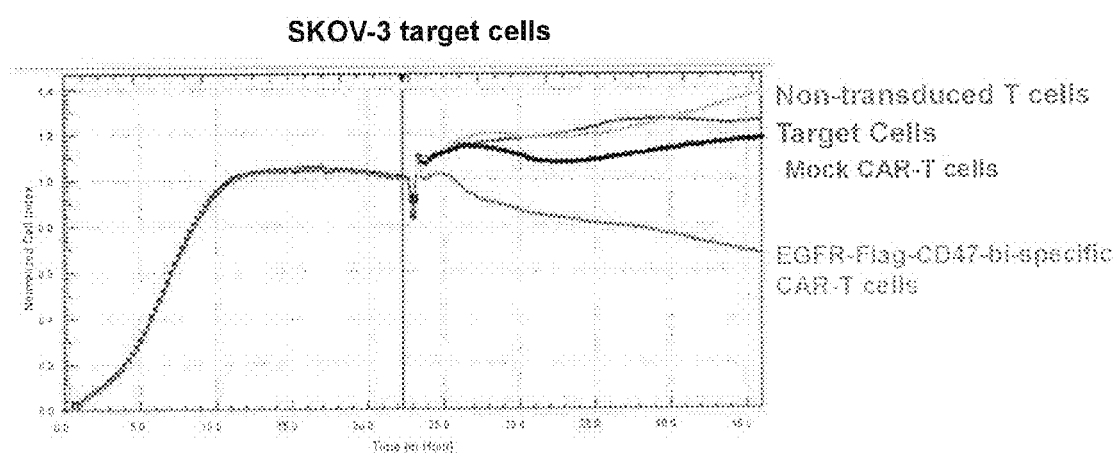

Bi-specific EGFR-CD47 CAR-T cells killed EGFR-negative MCF-7 cells demonstrating CD47-specific activity (FIG. 7). In addition, EGFR-CD47 CAR-T cells effective killed EGFR-positive and CD47-positive BxPC3 pancreatic cancer cells (FIG. 8A) and SKOV ovarian cancer cells (FIG. 8B). These data demonstrate the application of bispecific EGFR-CD47 CAR.

It is to be understood that the foregoing describes preferred embodiments of the present invention and that modifications may be made therein without departing from the scope of the present invention as set forth in the claims.

What is claimed is:

1. A chimeric antigen receptor fusion protein comprising from N-terminus to C-terminus:
   (i) a single-chain variable fragment (scFv) comprising VH and VL, wherein the scFv is against CD47,
   (ii) a transmembrane domain,
   (iii) a co-stimulatory domain, and
   (iv) an activating domain,
   wherein the scFv is derived from a humanized CD47 antibody and comprises the amino acid sequences of SEQ ID NOs: 11 and 12, linked by a linker.

2. The fusion protein of claim 1, wherein the scFv has the amino acid sequence of SEQ ID NO: 13.

3. The fusion protein according to claim 1, wherein the co-stimulatory domain is selected from the group consisting of CD28, 4-1BB, ICOS-1, CD27, OX-40, DAP10 and GITR.

4. The fusion protein according to claim 3, wherein the co-stimulatory domain is CD28.

5. The fusion protein according to claim 1, wherein the activating domain is CD3-zeta.

6. The fusion protein according to claim 1, which has the amino acid sequence of SEQ ID NO: 14.

7. The fusion protein according to claim 1, wherein (i) further comprises a second single-chain variable fragment (scFv) comprising a second VH and a second VL, wherein the second scFv is against EGFR.

8. The fusion protein according to claim 7, which has the amino acid sequence of SEQ ID NO: 17.

9. A nucleic acid sequence encoding the fusion protein of claim 1.

10. T cells modified to express the fusion protein of claim 1.

* * * * *

SEQUENCE LISTING

<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Asp Tyr Lys Asp Asp Asp Asp Lys
1               5

<210> SEQ ID NO 2
<211> LENGTH: 21
<212> TYPE: PRT
<213> ORGANISM: Homo sapiens

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 118
<212> TYPE: PRT
<213> ORGANISM: Mus musculus

<400> SEQUENCE: 3

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
        115

<210> SEQ ID NO 4
<211> LENGTH: 15
<212> TYPE: PRT
<213> ORGANISM: Artificial Sequence
<220> FEATURE:
<223> OTHER INFORMATION: synthetic

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 107
<212> TYPE: PRT
<213> ORGANISM: Mus musculus

<400> SEQUENCE: 5

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
                20                  25                  30

Leu His Trp Tyr Gln Gln Lys Ser His Glu Ser Pro Arg Leu Leu Ile
            35                  40                  45

Lys Phe Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
                100                 105

<210> SEQ ID NO 6
<211> LENGTH: 49
<212> TYPE: PRT
<213> ORGANISM: Homo sapiens

<400> SEQUENCE: 6

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
                20                  25                  30

Ala Gly Gly Ala Val His Thr Arg Gly Leu Asp Phe Ala Ser Asp Lys
            35                  40                  45

Pro

<210> SEQ ID NO 7
<211> LENGTH: 27
<212> TYPE: PRT
<213> ORGANISM: Homo sapiens

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 8
<211> LENGTH: 41
<212> TYPE: PRT
<213> ORGANISM: Homo sapiens

<400> SEQUENCE: 8

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 9
<211> LENGTH: 112
<212> TYPE: PRT
<213> ORGANISM: Homo sapiens -continued

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 495
<212> TYPE: PRT
<213> ORGANISM: Mus musculus

<400> SEQUENCE: 10

Met Ala Leu Pro Val Thr Ala Leu Leu Leu Pro Leu Ala Leu Leu Leu
1               5                   10                  15

His Ala Ala Arg Pro Ala Ser Glu Val Gln Leu Val Glu Ser Gly Gly
            20                  25                  30

Asp Leu Val Lys Pro Gly Gly Ser Leu Lys Leu Ser Cys Ala Ala Ser
        35                  40                  45

Gly Phe Thr Phe Ser Gly Tyr Gly Met Ser Trp Val Arg Gln Thr Pro
    50                  55                  60

Asp Lys Arg Leu Glu Trp Val Ala Thr Ile Thr Ser Gly Gly Thr Tyr
65                  70                  75                  80

Thr Tyr Tyr Pro Asp Ser Val Lys Gly Arg Phe Thr Ile Ser Arg Asp
                85                  90                  95

Asn Ala Lys Asn Thr Leu Tyr Leu Gln Ile Asp Ser Leu Lys Ser Glu
            100                 105                 110

Asp Thr Ala Ile Tyr Phe Cys Ala Arg Ser Leu Ala Gly Asn Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Pro Ala Thr Leu Ser Val Thr Pro Gly Asp Arg Val Ser
                165                 170                 175

Leu Ser Cys Arg Ala Ser Gln Thr Ile Ser Asp Tyr Leu His Trp Tyr
            180                 185                 190

Gln Gln Lys Ser His Glu Ser Pro Arg Leu Leu Ile Lys Phe Ala Ser
        195                 200                 205

Gln Ser Ile Ser Gly Ile Pro Ser Arg Phe Ser Gly Ser Gly Ser Gly
    210                 215                 220

Ser Asp Phe Thr Leu Ser Ile Asn Ser Val Glu Pro Glu Asp Val Gly
225                 230                 235                 240

Val Tyr Tyr Cys Gln Asn Gly His Gly Phe Pro Arg Thr Phe Gly Gly
                245                 250                 255

```
Gly Thr Lys Leu Glu Ile Lys Leu Glu Lys Pro Thr Thr Pro Ala
            260                 265                 270

Pro Arg Pro Pro Thr Pro Ala Pro Thr Ile Ala Ser Gln Pro Leu Ser
275                 280                 285

Leu Arg Pro Glu Ala Ser Arg Pro Ala Ala Gly Gly Ala Val His Thr
    290                 295                 300

Arg Gly Leu Asp Phe Ala Ser Asp Lys Pro Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Gln
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 11
<211> LENGTH: 118
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
            115
```

```
<210> SEQ ID NO 12
<211> LENGTH: 107
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Phe Ala Ser Gln Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly His Gly Phe Pro Arg
                85                  90                  95

Thr Phe Gly Gly Gly Thr Lys Val Glu Ile Lys
            100                 105

<210> SEQ ID NO 13
<211> LENGTH: 240
<212> TYPE: PRT
<213> ORGANISM: Homo sapiens

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Leu Thr Gln Ser Pro Ala Thr Leu
    130                 135                 140

Ser Leu Ser Pro Gly Glu Arg Ala Thr Leu Ser Cys Arg Ala Ser Gln
145                 150                 155                 160

Ser Ile Ser Asp Tyr Leu His Trp Tyr Gln Gln Lys Pro Gly Gln Ala
                165                 170                 175

Pro Arg Leu Leu Ile Tyr Phe Ala Ser Gln Arg Ala Thr Gly Ile Pro
            180                 185                 190

Ala Arg Phe Ser Gly Ser Gly Ser Gly Thr Asp Phe Thr Leu Thr Ile
        195                 200                 205
```

```
Ser Ser Leu Glu Pro Glu Asp Phe Ala Val Tyr Tyr Cys Gln Gln Gly
210                 215                 220

His Gly Phe Pro Arg Thr Phe Gly Gly Gly Thr Lys Val Glu Ile Lys
225                 230                 235                 240
```

<210> SEQ ID NO 14
<211> LENGTH: 495
<212> TYPE: PRT
<213> ORGANISM: Homo sapiens

<400> SEQUENCE: 14

```
Met Ala Leu Pro Val Thr Ala Leu Leu Leu Pro Leu Ala Leu Leu Leu
1               5                   10                  15

His Ala Ala Arg Pro Ala Ser Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Thr Phe Ser Gly Tyr Gly Met Ser Trp Val Arg Gln Ala Pro
    50                  55                  60

Gly Lys Gly Leu Glu Trp Val Ala Thr Ile Thr Ser Gly Gly Thr Tyr
65                  70                  75                  80

Thr Tyr Tyr Pro Asp Ser Val Lys Gly Arg Phe Thr Ile Ser Arg Asp
                85                  90                  95

Asn Ala Lys Asn Ser Leu Tyr Leu Gln Met Asn Ser Leu Arg Ala Glu
                100                 105                 110

Asp Thr Ala Val Tyr Tyr Cys Ala Arg Ser Leu Ala Gly Asn Ala Met
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Leu
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Ser Ile Ser Asp Tyr Leu His Trp Tyr
                180                 185                 190

Gln Gln Lys Pro Gly Gln Ala Pro Arg Leu Leu Ile Tyr Phe Ala Ser
            195                 200                 205

Gln Arg Ala Thr Gly Ile Pro Ala Arg Phe Ser Gly Ser Gly Ser Gly
    210                 215                 220

Thr Asp Phe Thr Leu Thr Ile Ser Ser Leu Glu Pro Glu Asp Phe Ala
225                 230                 235                 240

Val Tyr Tyr Cys Gln Gln Gly His Gly Phe Pro Arg Thr Phe Gly Gly
                245                 250                 255

Gly Thr Lys Val Glu Ile Lys Leu Glu Lys Pro Thr Thr Thr Pro Ala
                260                 265                 270

Pro Arg Pro Pro Thr Pro Ala Pro Thr Ile Ala Ser Gln Pro Leu Ser
            275                 280                 285

Leu Arg Pro Glu Ala Ser Arg Pro Ala Ala Gly Gly Ala Val His Thr
    290                 295                 300

Arg Gly Leu Asp Phe Ala Ser Asp Lys Pro Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
                340                 345                 350
```

-continued

Tyr Met Asn Met Thr Pro Arg Arg Pro Gly Pro Thr Arg Lys His Tyr
            355                 360                 365

Gln Pro Tyr Ala Pro Pro Arg Asp Phe Ala Ala Tyr Arg Ser Arg Val
        370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Gln
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 15
<211> LENGTH: 126
<212> TYPE: PRT
<213> ORGANISM: Homo sapiens

<400> SEQUENCE: 15

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Gly Pro Tyr Cys Ser Ser Thr Ser Cys Tyr Gly Ala
            100                 105                 110

Phe Asp Ile Trp Gly Gln Gly Thr Leu Val Thr Val Ser Ser
        115                 120                 125

<210> SEQ ID NO 16
<211> LENGTH: 108
<212> TYPE: PRT
<213> ORGANISM: Homo sapiens

<400> SEQUENCE: 16

Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Ser Tyr Phe Ala
            20                  25                  30

Ser Trp Tyr Gln Gln Lys Pro Gly Gln Ala Pro Thr Leu Val Met Tyr
        35                  40                  45

Ala Arg Asn Asp Arg Pro Ala Gly Val Pro Asp Arg Phe Ser Gly Ser
    50                  55                  60

```
Lys Ser Gly Thr Ser Ala Ser Leu Ala Ile Ser Gly Leu Gln Ser Glu
 65                  70                  75                  80

Asp Glu Ala Asp Tyr Tyr Cys Ala Ala Trp Asp Asp Ser Leu Asn Gly
                 85                  90                  95

Tyr Leu Phe Gly Ala Gly Thr Lys Leu Thr Val Leu
            100                 105

<210> SEQ ID NO 17
<211> LENGTH: 767
<212> TYPE: PRT
<213> ORGANISM: Homo sapien

<400> SEQUENCE: 17

Met Ala Leu Pro Val Thr Ala Leu Leu Leu Pro Leu Ala Leu Leu Leu
  1               5                  10                  15

His Ala Ala Arg Pro Ala Ser Glu Val Gln Leu Val Gln Ser Gly Ala
                 20                  25                  30

Glu Val Lys Lys Pro Gly Ser Ser Val Lys Val Ser Cys Lys Ala Ser
             35                  40                  45

Gly Gly Thr Phe Ser Ser Tyr Ala Ile Ser Trp Val Arg Gln Ala Pro
 50                  55                  60

Gly Gln Gly Leu Glu Trp Met Gly Gly Ile Ile Pro Ile Phe Gly Thr
 65                  70                  75                  80

Ala Asn Tyr Ala Gln Lys Phe Gln Gly Arg Val Thr Ile Thr Ala Asp
                 85                  90                  95

Glu Ser Thr Ser Thr Ala Tyr Met Glu Leu Ser Ser Leu Arg Ser Glu
            100                 105                 110

Asp Thr Ala Val Tyr Tyr Cys Ala Arg Glu Glu Gly Pro Tyr Cys Ser
            115                 120                 125

Ser Thr Ser Cys Tyr Gly Ala Phe Asp Ile Trp Gly Gln Gly Thr Leu
        130                 135                 140

Val Thr Val Ser Ser Gly Gly Gly Gly Ser Gly Gly Gly Gly Ser Gly
145                 150                 155                 160

Gly Gly Gly Ser Gln Ser Val Leu Thr Gln Asp Pro Ala Val Ser Val
                165                 170                 175

Ala Leu Gly Gln Thr Val Lys Ile Thr Cys Gln Gly Asp Ser Leu Arg
            180                 185                 190

Ser Tyr Phe Ala Ser Trp Tyr Gln Gln Lys Pro Gly Gln Ala Pro Thr
        195                 200                 205

Leu Val Met Tyr Ala Arg Asn Asp Arg Pro Ala Gly Val Pro Asp Arg
    210                 215                 220

Phe Ser Gly Ser Lys Ser Gly Thr Ser Ala Ser Leu Ala Ile Ser Gly
225                 230                 235                 240

Leu Gln Ser Glu Asp Glu Ala Asp Tyr Tyr Cys Ala Ala Trp Asp Asp
                245                 250                 255

Ser Leu Asn Gly Tyr Leu Phe Gly Ala Gly Thr Lys Leu Thr Val Leu
            260                 265                 270

Asp Tyr Lys Asp Asp Asp Asp Lys Gly Gly Gly Ser Gly Gly Gly Gly
        275                 280                 285

Gly Ser Gly Gly Gly Ser Asp Ile Val Met Thr Gln Ser Pro Ala
    290                 295                 300

Thr Leu Ser Val Thr Pro Gly Asp Arg Val Ser Leu Ser Cys Arg Ala
305                 310                 315                 320

Ser Gln Thr Ile Ser Asp Tyr Leu His Trp Tyr Gln Gln Lys Ser His
                325                 330                 335
```

```
Glu Ser Pro Arg Leu Leu Ile Lys Phe Ala Ser Gln Ser Ile Ser Gly
                340                 345                 350

Ile Pro Ser Arg Phe Ser Gly Ser Gly Ser Gly Ser Asp Phe Thr Leu
                355                 360                 365

Ser Ile Asn Ser Val Glu Pro Glu Asp Val Gly Val Tyr Tyr Cys Gln
            370                 375                 380

Asn Gly His Gly Phe Pro Arg Thr Phe Gly Gly Gly Thr Lys Leu Glu
385                 390                 395                 400

Ile Lys Gly Gly Gly Gly Ser Gly Gly Gly Gly Ser Gly Gly Gly Gly
                405                 410                 415

Ser Glu Val Gln Leu Val Glu Ser Gly Gly Asp Leu Val Lys Pro Gly
                420                 425                 430

Gly Ser Leu Lys Leu Ser Cys Ala Ala Ser Gly Phe Thr Phe Ser Gly
                435                 440                 445

Tyr Gly Met Ser Trp Val Arg Gln Thr Pro Asp Lys Arg Leu Glu Trp
                450                 455                 460

Val Ala Thr Ile Thr Ser Gly Gly Thr Tyr Thr Tyr Tyr Pro Asp Ser
465                 470                 475                 480

Val Lys Gly Arg Phe Thr Ile Ser Arg Asp Asn Ala Lys Asn Thr Leu
                485                 490                 495

Tyr Leu Gln Ile Asp Ser Leu Lys Ser Glu Asp Thr Ala Ile Tyr Phe
            500                 505                 510

Cys Ala Arg Ser Leu Ala Gly Asn Ala Met Asp Tyr Trp Gly Gln Gly
            515                 520                 525

Thr Ser Val Thr Val Ser Ser Leu Glu Lys Pro Thr Thr Thr Pro Ala
            530                 535                 540

Pro Arg Pro Pro Thr Pro Ala Pro Thr Ile Ala Ser Gln Pro Leu Ser
545                 550                 555                 560

Leu Arg Pro Glu Ala Ser Arg Pro Ala Ala Gly Gly Ala Val His Thr
                565                 570                 575

Arg Gly Leu Asp Phe Ala Ser Asp Lys Pro Phe Trp Val Leu Val Val
            580                 585                 590

Val Gly Gly Val Leu Ala Cys Tyr Ser Leu Leu Val Thr Val Ala Phe
            595                 600                 605

Ile Ile Phe Trp Val Arg Ser Lys Arg Ser Arg Leu Leu His Ser Asp
            610                 615                 620

Tyr Met Asn Met Thr Pro Arg Arg Pro Gly Pro Thr Arg Lys His Tyr
625                 630                 635                 640

Gln Pro Tyr Ala Pro Pro Arg Asp Phe Ala Ala Tyr Arg Ser Arg Val
                645                 650                 655

Lys Phe Ser Arg Ser Ala Asp Ala Pro Ala Tyr Gln Gln Gly Gln Asn
                660                 665                 670

Gln Leu Tyr Asn Glu Leu Asn Leu Gly Arg Arg Glu Glu Tyr Asp Val
            675                 680                 685

Leu Asp Lys Arg Arg Gly Arg Asp Pro Glu Met Gly Gly Lys Pro Gln
            690                 695                 700

Arg Arg Lys Asn Pro Gln Glu Gly Leu Tyr Asn Glu Leu Gln Lys Asp
705                 710                 715                 720

Lys Met Ala Glu Ala Tyr Ser Glu Ile Gly Met Lys Gly Glu Arg Arg
                725                 730                 735
```

```
Arg Gly Lys Gly His Asp Gly Leu Tyr Gln Gly Leu Ser Thr Ala Thr
            740                 745                 750

Lys Asp Thr Tyr Asp Ala Leu His Met Gln Ala Leu Pro Pro Arg
            755                 760                 765
```